US007468150B2

(12) United States Patent
Alocilja et al.

(10) Patent No.: US 7,468,150 B2
(45) Date of Patent: Dec. 23, 2008

(54) SYNTHESIS OF CONDUCTO-MAGNETIC POLYMERS AS NANO-TRANSDUCERS IN BIOSENSOR DESIGN

(75) Inventors: Evangelyn C. Alocilja, East Lansing, MI (US); John C. Zhou, Northville, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 11/525,425

(22) Filed: Sep. 22, 2006

(65) Prior Publication Data

US 2007/0069186 A1 Mar. 29, 2007

Related U.S. Application Data

(60) Provisional application No. 60/720,601, filed on Sep. 26, 2005.

(51) Int. Cl.
*H01B 1/00* (2006.01)
*C12N 13/00* (2006.01)

(52) U.S. Cl. ......................... 252/500; 252/511; 422/28; 435/4; 435/173.8; 442/110; 536/23.1

(58) Field of Classification Search ................. 252/500, 252/511; 528/422; 524/108; 435/173.8, 435/4; 210/656; 422/28; 536/23.1; 442/110
See application file for complete search history.

(56) References Cited

U.S. PATENT DOCUMENTS

| | | | | |
|---|---|---|---|---|
| 5,776,370 | A * | 7/1998 | Afzali-Ardakani et al. | 252/500 |
| 5,843,741 | A * | 12/1998 | Wong et al. | 435/173.8 |
| 6,592,814 | B2 * | 7/2003 | Wilcox et al. | 422/28 |
| 6,752,936 | B2 * | 6/2004 | Baozong et al. | 252/511 |
| 2001/0041485 | A1 * | 11/2001 | Zhao et al. | 442/110 |
| 2005/0098501 | A1 * | 5/2005 | Leiser et al. | 210/656 |
| 2006/0035208 | A1 * | 2/2006 | Roget et al. | 435/4 |
| 2006/0041110 | A1 * | 2/2006 | Samuelson et al. | 536/23.1 |

* cited by examiner

*Primary Examiner*—Lorna M Douyon
*Assistant Examiner*—Khanh Tuan Nguyen
(74) *Attorney, Agent, or Firm*—Ian C. McLeod

(57) ABSTRACT

A conductive polymer of polyaniline (PANi), tetracyanoquinodimethane (TCNQ) and a transferrin family member. The conductive polymer can be used in conductometric assays, including biosensor devices. One particular transferrin family member provided in the polymer is lactoferrin.

6 Claims, 3 Drawing Sheets

SYNTHESIS OF CONDUCTO-MAGNETIC POLYMERS AS NANO-TRANSDUCERS IN BIOSENSOR DESIGN

CROSS-REFERENCE TO RELATED APPLICATIONS

This application claims benefit of Provisional Application No. 60/720,601, filed Sep. 26, 2005, which is incorporated herein by reference in its entirety.

STATEMENT REGARDING GOVERNMENT RIGHTS

This invention was funded in part by the Department of Homeland Security through the National Center for Food Protection and Defense, Homeland Security Grant No. R9106007104. The U.S. Government has certain rights to this invention.

STATEMENT REGARDING FEDERALLY SPONSORED RESEARCH OR DEVELOPMENT

Not Applicable.

BACKGROUND OF THE INVENTION

1. Field of the Invention

The present invention relates to novel polymers having conductive polyaniline, tetracyanoquinodimethane and a transferrin family member that can be used in conductimetric biosensors. One member of the transferrin family provided in the polymer is lactoferrin.

2. Description of Related Art

Polymers, once used for insulating purposes, have gained prominence for electrical conductivity, among other novel traits such as magnetism and biodegradability. The appellation "synthetic metals" has been duly given to these polymers that exemplify the conductive/magnetic properties of the metallic inorganics (e.g. iron), as well as the flexibility and lightness of plastics.

The importance of conductive polymers alone is perhaps best demonstrated by the awarding of the 2000 Nobel Prize in chemistry for effort in the field. Conducting polymers can be utilized in diverse areas ranging from corrosion protection to microwave shielding (M. Gerard, A. Chaubey, and B. D. Malhotra. Application of conducting polymers to biosensors. *Biosensors & Bioelectronics* (2002), 17, 345). Analytical chemistry and chemical/biological sensors are significant areas of applications as well (Gerard et al. Ibid.). The conductive properties of the synthetic metals arise from the π-electron backbone and the single/double bonds of the π-conjugated system alternating down the polymer chain (Gerard et al. Ibid.). Some conducting polymeric structures include polyaniline (PANi), polypyrrole, polyacetylene, and polyphenylene (Gerard et al. Ibid.). Polyaniline, in particular, has been studied thoroughly because of its stability in fluid form, conductive properties, and strong bio-molecular interactions (Z. Muhammad-Tahir, and E. C. Alocilja. A disposable biosensor for pathogen detection in fresh produce samples. *Biosystems Engineering* (2004), 88, 145).

Fully organic polymers displaying magnetism are in high demand for their potentially tremendous applications in varying fields: electronic, magnetic, and photonic/photronic devices including information storage, magnetic imaging, static and low frequency magnetic shielding, and magnetic induction (A. J. Epstein, and J. S. Miller. Molecule- and polymer-based magnets, a new frontier. Synthetic Metals (1996), 80, 231). Indeed, organic magnets represent a completely new class of materials. So far, however, limited work has been done on the synthesis of conducting-magnetic polymers (F. Yan, G. Xue, J. Chen, and Y. Lu. Preparation of a conducting polymer/ferromagnet composite film by anodic-oxidation method. *Synth Met* (2001), 123, 17). Much of the work has involved the simple mixing of inorganic ferromagnetic powder with conducting polymer powder. This approach raises the issue of incompatibility with inorganic and organic phases as well as the difficulty in working with such a blend. A promising organic magnet derived from PANi, however, has been reported recently (N. A. Zaidi, S. R. Giblin, I. Terry, and A. P. Monkman. Room temperature magnetic order in an organic magnet derived from polyaniline. *Polymer* (2004), 45, 5683). This polymer, named PANiCNQ, is a result of the synthesis from PANi and tetracyanoquinodimethane (TCNQ), an acceptor molecule. Room temperature magnetization was observed in PANiCNQ only after a three month period.

Besides being electrically conductive and/or magnetic, organic polymers with biodegradable attributes can be appreciably employed in tissue engineering by regulating cellular activities such as cell migration, cell adhesion, DNA synthesis, and protein secretion (G. Shi, M. Rouabhia, Z. Wang, L. H. Dao, and Z. Zhang. A novel electrically conductive and biodegradable composite made of polypyrrole nanoparticles and polylactide. *Biomaterials* (2004), 25, 2477). Implantable biosensors may require biodegradability and biocompatibility as well. One promising biodegradable polymer is β-carotene, a source of vitamin A. It has large, delocalized π-electron systems over a chain of roughly 20 carbon atoms connected by bonds (G. Leatherman, E. N. Durantini, D. Gust, T. A. Moore, A. L. Moore, S. Stone, Z. Zhou, P. Rez, Y. Z. Liu, and S. M. Lindsay. Carotene as a molecular wire: Conducting atomic force microscopy. *J. Phys. Chem.* B (1999), 103, 4006). Furthermore, the molecule can be oxidized electrochemically, thus implying β-carotene may have conductive properties (Leatherman et al. Ibid.) . As of yet unexplored polymeric composites with β-carotene and other polymers represent areas of investigation for feasible biodegradable and biocompatible materials with conductive properties.

A significant approach to test novel polymers with conductive, magnetic, biodegradable, and/or biocompatible traits is the biosensor, an analytical device capable of pathogen detection. Organic conductive polymers act as electrochemical transducers to transform biological signals to electric signals. Conductive polymers that also demonstrate magnetic properties are advantageous in biosensors. It is possible to guide biosensors within a body or organism by applying external magnets (e.g. glucose biosensors in diabetics). Furthermore, the polymers may be concentrated by drawing the sensors together with magnets, thereby increasing the yield of polymers conjugated with antibodies, and strengthening the output electrical signal.

Statistics has shown that pathogens result in an estimated 14 million illnesses, 60,000 hospitalizations, 1,800 deaths, and cost approximately $2.9-$6.7 billion in the United States each year due to food-borne diseases (P. S. Mead, L. Slutsker, V. Dietz, L. F. McCaig, J. S. Bresee, C. Shapiro, P. M. Griffin, and R. V. Tauxe. Food-related illness and death in the United States. *Emerg Infect Dis* (1999), 5, 607; J. C. Buzby, T. Roberts, C. T. J. Lin, and J. M. MacDonald. Bacterial foodborne disease: Medical costs and productivity losses. Agricultural Economics Report No. 741:100. USDA Economic Research Service, Washington, D.C., USA (1996)). Furthermore, possible bioterror threats after Sep. 11, 2001 has presented urgent needs of biosensors for surveillance of foods to prevent the contamination of food supplies (World Health Organization (WHO), Terrorist threats to food: Guidance for establishing and strengthening prevention . . . . WHO Food Safety Dept., Geneva, Switzerland (2002)). Of these numerous food-borne pathogens, *Bacillus cereus* has garnered notice as bacteria that can cause two types of food poisoning: a diarrheal type, and an emetic type (P. E. Granum, and T. Lund. *Bacillus cereus* and its food poisoning toxins. *FEMS Microbiology Letters* (1997), 157, 223). The former leads to diarrhea while the latter results in vomiting (Granum et al. Ibid.). The ubiquitous nature of the *B. cereus* pathogen is demonstrated by its status as a common soil saprophyte and association with foods, primarily plants, but also meats, eggs, and dairy products (Granum et al. Ibid.). It was implicated in a third of all cases of food poisoning in Norway (1988-1993), 47% in Iceland (1985-1992), and 22% in Finland (1992) (Granum et al. Ibid.). Furthermore, recent research has concluded that *Bacillus anthracis* and *Bacillus cereus* are of the same species (E. Helgason, O. A. Okstad, D. A. Caugant, H. A. Johansen, A. Fouet, M. Mock, I. Hegna, and A. Kolsto. *Bacillus anthracis, Bacillus cereus,* and *Bacillus thuringiensis*—One species on the basis of genetic evidence. *Applied and Environmental Microbiology* (2000), 66, 2627). *B. anthracis* is responsible for the lethal disease anthrax, an agent in biological terrorism/warfare (Helgason et al. Ibid.). Thus, detection and defense using biosensors against *B. cereus* may accurately model and lead to heightened security with respect to *B. anthracis.*

Identification of pathogens by conventional methods, however, necessitates manual work and anywhere from 24 to 48 hours of incubation time (Z. Muhammad-Tahir, and E. C. Alocilja. Fabrication of a disposable biosensor *Escherichia coli* 0157:H7 Detection. *IEEE Sensors Journal* (2003), 3, 345). Biosensors that are rapid, portable, accurate, sensitive and easy to use are crucial for optimal detection of pathogens, including *B. cereus*. Electrochemical immunosensors, one type of biosensor, utilize antibodies as a biological sensing element connected to an electrochemical transducer (the organic conductive polymer) (Z. Muhammad-Tahir, and E. C. Alocilja. A disposable biosensor for pathogen detection in fresh produce samples. *Biosystems Engineering* (2004), 88, 145). An advantage of utilizing antibodies is that the employment of antibodies specific to other pathogens can result in biosensors effective for said pathogens (e.g. *E. coli* 0157:H7). Thus, the biosensor is not limited in effectiveness to just *B. cereus.*

SUMMARY OF THE INVENTION

The present invention provides a polymer which comprises an electrically conductive reaction product of an emeraldine polyaniline (PANi), tetracyanoquinodimethane (TCNQ) and a transferrin family member. In further embodiments, the transferrin family member is lactoferrin. In further embodiments, the polymer has magnetic properties. In still further embodiments, the polyaniline is provided as an emeraldine base or an emeraldine salt.

The present invention provides a process for preparing a polymer that is a reaction product of an emeraldine polyaniline (PANi), tetracyanoquinodimethane (TCNQ) and a transferrin family member which comprises: reacting the PANi and the TCNQ in a solvent at a temperature between about 20° C. and 150° C.; adding the transferrin family member to the solvent with further heating at a temperature of between about 20° C. and 150° C.; and removing the polymer from the solvent. In further embodiments, the transferrin is lactoferrin. In still further embodiments, the solvent is N-methyl-2-pyrollidinone (NMP). In further embodiments, the process further comprises the step of aging the polymer after step (c) for a time so that the polymer has magnetic properties. In still further embodiments, the polymer is removed from the solvent in step (c) by filtration. In still further embodiments, the polymer also comprises β-carotene.

The present invention provides a conductometric assay wherein a conductive polymer is bound to a capture reagent binding an analyte of interest, the improvement which comprises using a polymer comprising a reaction product of an emeraldine polyaniline (PANi), tetracyanoquinodimethane (TCNQ) and a transferrin family member as the conductive polymer. In further embodiments, the transferrin family member is lactoferrin.

BRIEF DESCRIPTION OF DRAWINGS

(FIGS. 2A, 2C, 2E) are mass magnetization as a function of temperature; (FIGS. 2B, 2D, 2F) are mass magnetization as a function of magnetic field strength.

FIGS. 3A, 3C, and 3E are average normalized resistance drops; FIGS. 3B, 3D, and 3F are resistance drops separated by time.

DESCRIPTION OF PREFERRED EMBODIMENTS

Figure 1:
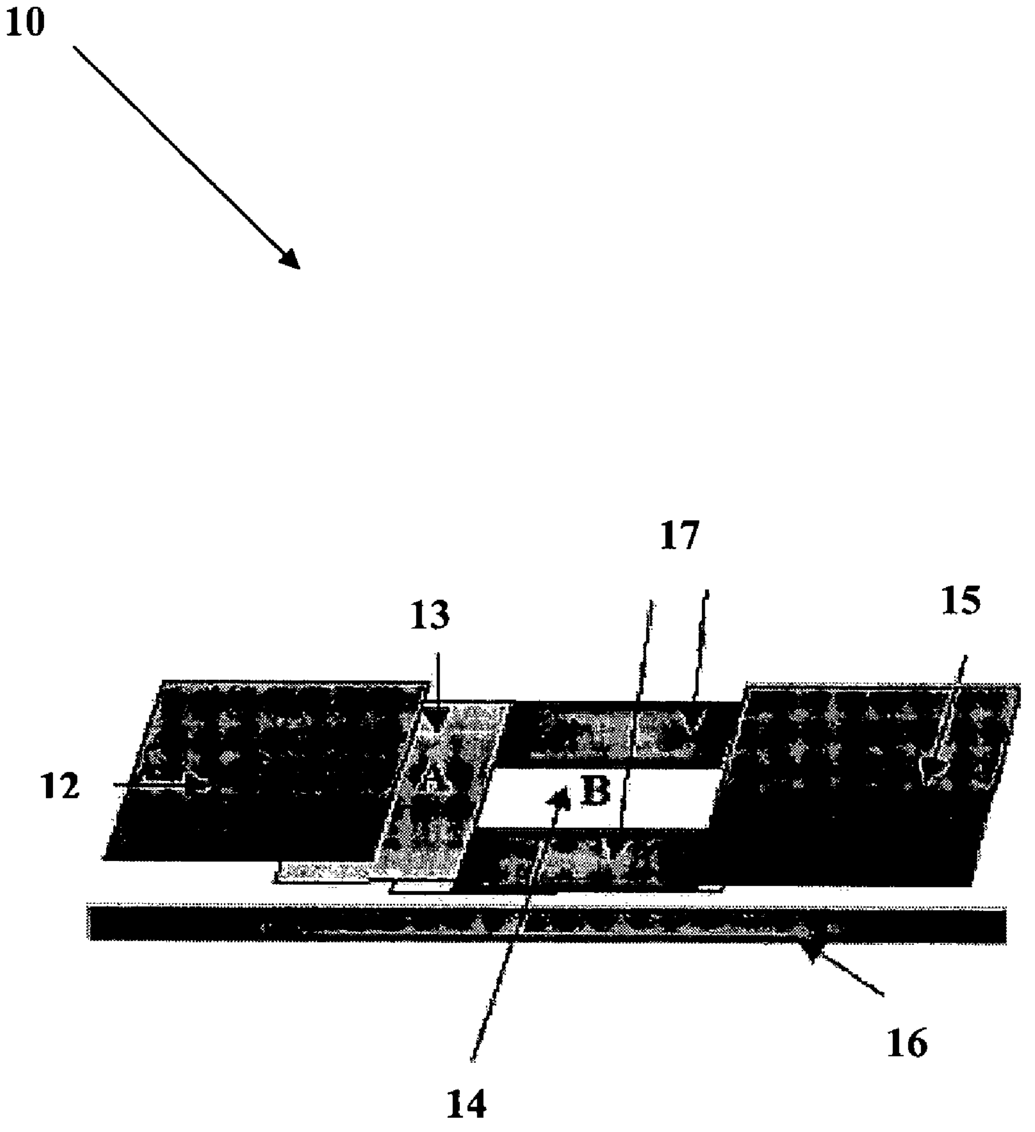
FIG. 1 is a schematic illustration of a biosensor 10 that can incorporate the conductive polymers of the present invention.

All patents, patent applications, government publications, government regulations, and literature references cited in this specification are hereby incorporated herein by reference in their entirety. In case of conflict, the present description, including definitions, will control.

The term "analyte" refers to a substance to be detected by an assay device. The term encompasses whole cells, such as microorganisms including, but not limited to *B. cereus, B. anthracis,* and *E. coli*. The term also includes both small and large molecules of interest, such as, but not limited to, DNA, enzymes, proteins, sugars, and other biochemicals or other chemicals.

The term "capture reagent with the conductive moiety" as used herein refers to a fluid mobile reagent which selectively binds to the analyte and which is bound to or is a moiety of the conductive polymer.

The term "immobile capture reagent" refers to a reagent which is bound to or is a moiety of a conductimetric assay device and which also selectively binds to the analyte.

The term "capture reagent" includes any molecule that selectively binds to the analyte of interest. The term includes, but is not limited to, selective antibodies, DNA, enzymes, lectins, proteins and chemicals which can bind to the analyte.

The term "conductometric assay" as used herein refers to any conductometric type assay known in the art. The term "conductometric" means that a signal is measured by means of a complex of an analyte linked directly or indirectly through a capture reagent to a conductive polymer. One example is provided as a conductimetric biosensor device as described in U.S. Patent Application Publication No. 2003/

0153094 to Alocilja et al. (U.S. patent application Ser. No. 10/074,499, filed Feb. 13, 2002), which is incorporated herein by reference in its entirety. The described biosensor can be modified, as described herein, to incorporate the conductive polymers of the present invention.

The term "conductive polymer" as used herein refers to a polymer capable of conducting electricity.

The term "PANi" as used herein refers to polyaniline.

The term "TCNQ" as used herein refers to tetracyanoquinodimethane.

The term "PANiCNQ" as used herein refers to a polymer produced from polyaniline (PANi) and acceptor molecule tetracyanoquinodimethane (TCNQ). Zaidi et al. (N. A. Zaidi, et al., "Room temperature magnetic order in an organic magnet derived from polyaniline", *Polymer* 45 5683-5689 (2004)), incorporated herein by reference in its entirety, describes the synthesis and characterization of PANiCNQ.

The term "PANiCNQ-Lactoferrin" or "PANiCNQ+Lactoferrin" is one embodiment of a conductive polymer of the present invention. It is produced from polyaniline (PANi), tetracyanoquinodimethane (TCNQ) and lactoferrin.

The term "transferrin" or "transferrin family member" as used herein refers to any of the group of homologous non-heme, glycoproteins with an approximate molecular weight of about 76,000 to about 81,000 capable of binding iron. (Merck Index, Thirteenth Edition (2001)). One example of a member of the transferrin family is lactoferrin. The term applies to a transferrin family member from any known organism, such as a mammal in the case of lactoferrin, having such iron-binding glycoproteins. Some examples of transferrins encompassed by the term include those proteins having sequences set forth in accession nos. A19780, A38725, AAA27820, AAA29338, AAA30958, AAA61142, AAB08440, AAB19439, AAB22049, AAB28966, AAB28967, AAB30760, AAB30762, AAB35968, AAB84034, AAB97880, AAC26078, AAD18032, AAF03084, AAH12313, AAH22986, AAH59367, AAH92046, AAM46784, AA039761, AAP94279, AAQ02339, AAQ02340, AAQ62963, AAT08022, AAW70172, AAY21643, AAY21644, ABC86975, ABC86976, ABC86977, ABC86978, ABC86979, ABD46825, ABI31834, AH004540, BAA07458, BAA10901, BAA84097, BAA84098, BAA84103, BAD27263, CAB82889, CAC19468, CAC42228, CAC59953, CAC59954, NP_001011572, NP_001013128, NP_001037014, NP_001054, NP_598738, NP_803450, and XP_516762 at the National Center for Biotechnology Information (National Library of Medicine, NIH). Some examples of lactoferrins encompassed by the term include those proteins having sequences set forth in accession nos. AAA21722, AAA30609, AAA30610, AAA30616, AAA30617, AAA31059, AAA31102, AAA39427, AAA59511, AAA86665, AAA97958, AAB24877, AAB33184, AAB57795, AAB60324, AAB62030, AAC34369, AAC77463, AAK66815, AAK66816, AAK66817, AAK66818, AAL40161, AAN11304, AAN75578, AAN84790, AAO14686, AAP70487, AAP82939, AAR12276, AAV92909, AAW71443, ABC67448, ABF69103, ABF69104, ABF69105, ABF69106, ABG75883, ABG75884, ABG75885, ABG75886, ABG75887, ABG75888, ABH01068, ABH01069, ABH01070, ABH01071, ABH01077, ABH01079, ABH01080, BAA13633, BAB03470, CAA06441, CAA09407, CAA55517, CAB53387, CAH04693, JC2323, and NP_002334 at the National Center for Biotechnology Information (National Library of Medicine, NIH).

The objective of the examples herein was two-fold: first, to synthesize novel polymers/nanocomposites; and second, to demonstrate their application in an electrochemical sandwich biosensor for *B. cereus* detection. Organic polymers were synthesized from PANi, TCNQ, and lactoferrin, and their conductivities and magnetic properties were characterized in the present application. The introduction of Lactoferrin, a 703 amino acid glycoprotein isolated from milk, was intended to augment the magnetization of the polymers. Lactoferrin can bind metal ions in exocrine secretions such as bile, pancreatic juice, and small intestinal secretions (P. F. Levay, and M. Viljoen. Lactoferrin: a general review. Haemtologica (1995), 80, 252). Furthermore, organic materials were synthesized from β-carotene and PANi and their conductivities as well as biodegradability were tested. PANiCNQ, PANiCNQ-Lactoferrin, and β-carotene+PANi emeraldine salt, were utilized as transducers in conductometric biosensors, whereupon the performances of the biosensors were assessed in terms of sensitivity. The effectiveness of detecting the *B. cereus* pathogen was demonstrated.

Materials and Methods.

Synthesis and characterization of PANiCNQ and related compounds: An amount (× grams) of emeraldine base form of PANi (MW: 65,000, FW: 93.31, Sigma-Aldrich) was dissolved in 10×mL of N-methyl-2-pyrollidinone (NMP, Sigma-Aldrich). TCNQ ($C_{12}H_4N_4$, FW: 204.19) was added to the mixture with a 2:1 mole ratio with respect to the aniline monomer of PANi. At this point, the mixture was blue/green in color. For PANiCNQ-Lactoferrin, ten milligrams (10 mg) of Lactoferrin (Sigma-Aldrich) was added at this point. After heating at 150° C. and spinning with a magnetic stirrer over night, the solution changed color to red/black. The solution was filtered through vacuum and buchner funnel the following day and then stored. PANiCNQ was stored for 3 weeks while PANiCNQ-Lactoferrin was stored for four weeks. Afterwards, NMP was removed by evaporation. The resulting black solid was broken up using mortar and pestle to form a fine powder. Compounds similar to PANiCNQ were synthesized correspondingly. For example, emeraldine base PANi was replaced by emeraldine salt in one sample.

In order to characterize PANiCNQ and related compounds, several methods were utilized. First, the DC SQUID (Superconducting Quantum Interference Device) magnetometer was used to measure magnetization of solid PANiCNQ after 3 weeks and the emeraldine base (control). Absorbance checks using spectrophotometer were performed on PANiCNQ in solution. Conductivities in solution of PANiCNQ were gauged by Acorn® TDS 5 Meter.

β-carotene nanocomposites: To create β-carotene nanocomposites, the use of an appropriate solvent was crucial. Acetone, toluene, kwik-dri, and tetrahydrofuran (THF) were tested. The solubility of β-carotene in kwik-dri, a non-aromatic industrial solvent similar to toluene, was crudely determined. Solutions of β-carotene nanocomposites were characterized by absorbance checks and conductivity measurements. Furthermore, the degradability of β-carotene in toluene was demonstrated by absorbance measurements over time. Mixtures of β-carotene with PANi emeraldine salt and various other PANi-derived polymers are attained forming a variety of other composites.

Biosensor fabrication: The biosensor 10 is a careful assorting of pads (application pad 12, conjugate pad 13, capture pad 14, and absorption pad 15) resting on a copper wafer 16 as a platform that acts as a structural support as shown in the schematic of FIG. 1. In the biosensor 10 illustrated in FIG. 1, the application pad 12 is 15×5 $mm^2$, the conjugate pad 13 is 10×5 $mm^2$, the capture pad 14 is 20×5 $mm^2$, the electrodes 17 are 20×2 $mm^2$, and the absorption pad 15 is 20×5 $mm^2$, however the biosensor is not limited to these dimensions.

Conjugation of antibodies to conductive polymer: In order to attach the antibodies to the conductive polymer, 800 μl of *B. cereus* antibody (0.15 mg/ml) was added to 8 ml of conductive polymer solution and left to react for 45 minutes to provide the capture reagent with the conductive moiety. One ml of Tris buffer containing 0.1% casein was introduced as a blocking reagent such that antibodies would not bind to the polymer strands afterwards.

Membrane construction: Four types of membranes were prepared: the application pad 12 membrane, conjugate pad 13 membrane, capture pad 14 membrane, and absorption pad 14 membrane. The application pad 12 membrane, where the bacteria sample is placed, was constructed by cutting sample pads (Millipore) into 6 cm strips. The absorption pad 15 membrane (Millipore), where the sample eventually flows, was similarly made. The conjugate pad 13 (glass fiber membranes, Millipore) was cut into 6 cm strips and then soaked in the *B. cereus* antibody conjugated with conducting polymer (as the capture reagent with the conductive moiety) and left to dry.

The capture pad 14 is where the flowing antibody-antigen-conducting polymer complex creates a bridge along the silver electrodes 17. It was assembled by cutting nitrocellulose membranes (Millipore) into 6 cm strips. The membranes were then washed in distilled water and by 10% methanol to cleanse the surface. After drying off for 30 minutes, the membranes were washed with 0.5% (v/v) glutaraldehyde, which leads to greater binding success. Following another drying off period (60 minutes) 0.5 mg/ml of *B. cereus* antibodies as an immobile capture reagent were applied on the membrane. The membranes were subsequently wrapped in parafilm and incubated for 60 min whereupon they were washed with 100 mM tris buffer with 0.1% (v/v) tween-20 to extricate the unbound antibodies. The prepared membranes were then incubated one last time for 45 minutes before being stored at 4° C.

Testing of the Biosensor.

Preparing and counting bacteria: *B. cereus* bacteria was obtained from stock solution present in the lab (a certified Biological Safety Level II laboratory). On the day preceding testing of the biosensor, bacteria isolates were inoculated from the stock culture using a 10 μl loop. The bacteria were then cultured and incubated in 10 ml nutrient broth for 24 hours at 37° C., thus forming new stock culture. To obtain bacteria of differing concentrations, cultures were serially diluted in 0.1 % peptone water such that there were seven ten-fold dilution. Testing using diluted bacteria provided a means of determining the detection limit of the biosensor. To determine the cell concentrations of bacteria (CFU/ml), about 1 ml of *B. cereus* bacteria was surface plated onto Standard Plate Count agar. After incubation at 37° C. overnight, the number of colonies was counted and the appropriate dilution factor was taken into consideration.

Signal detection and processing: The conductometric biosensor 10 was connected to a BK multimeter Model AK-2880A (Worcester, Mass.), whereupon the resistance across the electrodes 17 was initially infinite. After 0.1 ml of the sample (serially diluted bacteria or blank) was pipetted onto the sample application pad 12, a numerical resistance was shown. For every two (2) minutes afterwards, up to a total of eight (8) minutes, the resistance across the electrodes 17 of the biosensor 10 was recorded. Three trials were performed for each dilution of bacteria and the blank (0.1% peptone water). It was observed that the signal varied considerably during the first minute as the sample flowed from the sample application pad 12 through the conjugate pad 13 and capture pad 14, and into the absorption pad 15 by capillary action. The signal, however, stabilized soon afterwards. Past about eight (8) minutes, it was found that the signal decreased, most likely due to drying of the membrane of the capture pad 14.

As stated, the signal was measured and analyzed in the form of resistance for the sensor testing. It is of importance to note, however, that resistance (ohms, Ω) is the inverse of conductance (siemens, S), the unit of choice in characterizing polymers (e.g. PANiCNQ). Signal was evaluated by taking the resistance drop between the sample (diluted bacteria) and the blank. It was expected that resistance from the blank would be higher than the resistance from the sample, due to the conductivity provided by the antibody-antigen-conducting polymer complex.

Data analysis: Data analysis was performed using single factor analysis of variance (ANOVA). It was assumed that the biosensors were physically identical. Signal results were deemed statistically significant when the P-value was $<0.05$ (demonstrating a 95% confidence interval).

Results.

The conductivities of synthesized polymers are shown in Table 1.

TABLE 1

Conductivities of polymers and nanocomposites in solution measured using the Acorn ® TDS 5 Meter (Oakton)

| Compound Name | Conductivity (μS) | Compound Name | Conductivity (μS) |
|---|---|---|---|
| Pure PANiCNQ | $1.549 * 10^3$ | Kwik-dri | 0.1 |
| 1-Methyl-2-pyrrolidinone (NMP) | 0.975 | Kwik-dri + β-carotene | 0.15 |
| PANi Base (NMP) | 3.875 | Tetrahydrofuran (THF) | ~0 |
| PANi Base (NMP) after heating overnight | 4.55 | THF + β-carotene | ~0 |
| PANi Salt + TCNQ (NMP) | $1.540 * 10^3$ | Phosphate buffer + 10% DMF | $1.129 * 10^4$ |
| Pure PANiCNQ (3 weeks later) | $1.355 * 10^3$ | PANi Salt (10% DMF) | $1.3015 * 10^4$ |

TABLE 1-continued

Conductivities of polymers and nanocomposites in solution measured using the Acorn ® TDS 5 Meter (Oakton)

| Compound Name | Conductivity (μS) | Compound Name | Conductivity (μS) |
|---|---|---|---|
| PANiCNQ + Lactoferrin | 1.709 * $10^3$ | β-carotene (THF) + PANi (10% DMF) | 2.500 * $10^3$ |
| PANiCNQ + Lactoferrin (3 weeks later) | 1.697 * $10^3$ | PANi SALT (NMP), β-carotene (THF) | 5.51 * $10^1$ |
| PANiCNQ + Lactoferrin, β-carotene (THF) | 1.387 * $10^3$ | PANi SALT (NMP), β-carotene (THF) after 2 days | 1.16 * $10^2$ |

Figure 2A:
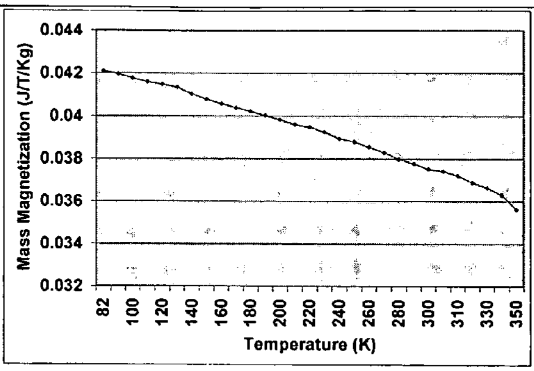
FIGS. 2A to 2F are graphs showing DC squid magnetization measurements on PANiCNQ (2A, 2B), PANiCNQ-Lactoferrin (FIGS. 2C, 2D), and PANi emeraldine base (control, FIGS. 2E, 2F)
Figure 2B:
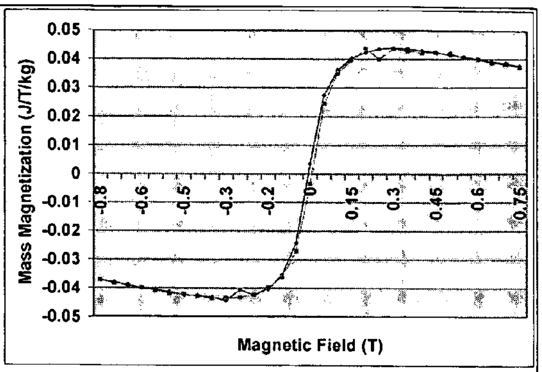

Magnetic diagrams: DC SQUID magnetometer measurements demonstrate the magnetic properties of PANiCNQ, PANiCNQ-Lactoferrin as well as of the PANi emeraldine base (control). A sample of PANiCNQ (3 weeks old, mass 0.16 g) was analyzed by SQUID from 350 K down to 90 K at 0.75 T to produce a graph relating magnetization with temperature (FIG. 2A). Furthermore, at 300 K (room temperature), the magnetic field was altered from 0.75 T to −0.75 T and then back again (FIG. 2B) creating a graph relating magnetization with magnetic field strength. PANiCNQ-Lactoferrin (4 weeks old) was investigated from 350 K to 3 K at 0.75 T to produce FIG. 2C and from 1 T to −1 T at 300 K to produce FIG. 2D. A sample of PANi emeraldine base was analyzed in the same manner creating FIG. 2E and FIG. 2F.

Figure 3A:
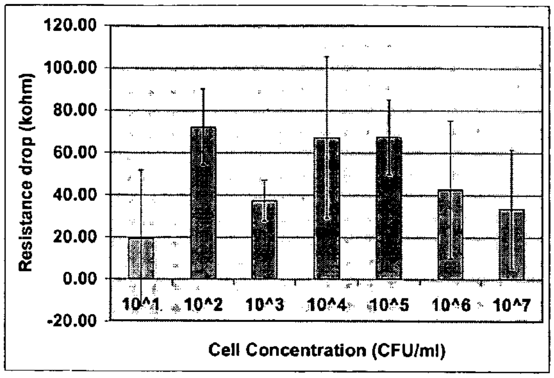
FIGS. 3A to 3F are graphs showing biosensor performance of antibodies conjugated with PANiCNQ (FIGS. 3A, 3B), PANiCNQ-Lactoferrin (FIGS. 3C, 3D), β-carotene and PANi emeraldine salt (FIGS. 3E, 3F)
Figure 3B:
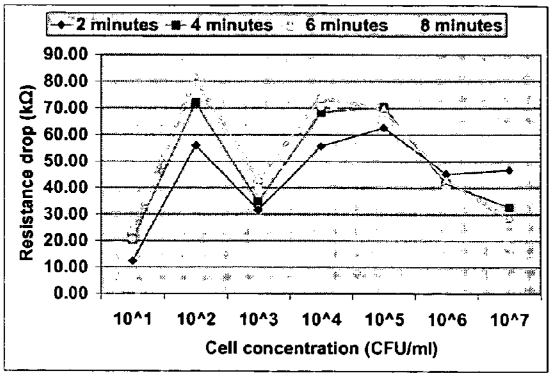
Figure 3C:
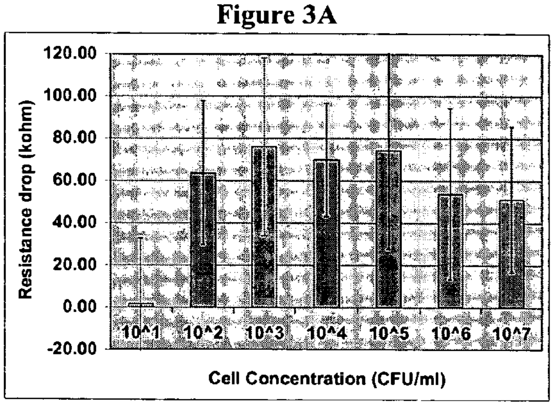
Figure 3D:
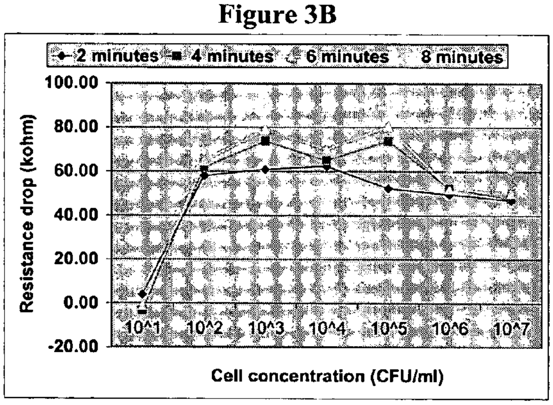
Figure 3E:
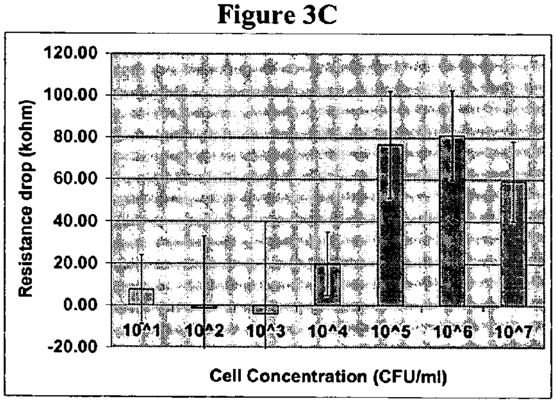
Figure 3F:
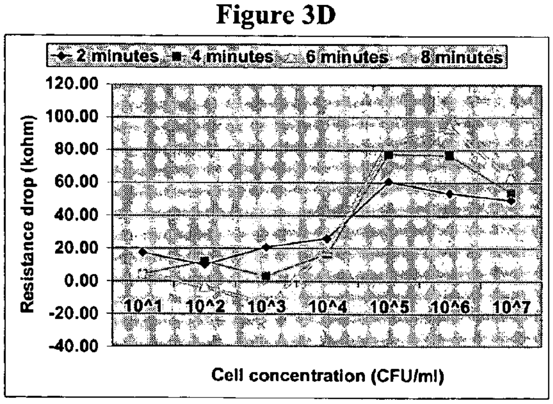

Sensitivity of biosensors: FIG. 3 demonstrates the sensitivity of the biosensor when the antibodies were conjugated with differing polymers. Signals were an average of three readings every two (2) minutes for eight (8) minutes. For the sensor having antibodies conjugated with PANiCNQ, signal responses to *B. cereus* were significantly different from the control at $10^2$ CFU/ml and higher (FIG. 3A, FIG. 3B). For the biosensor having antibodies conjugated with PANiCNQ and Lactoferrin, signal responses were also significantly different from the control at $10^2$ CFU/ml and higher (FIG. 3C, FIG. 3D) . For the biosensor having antibodies conjugated with β-carotene (THF) and PANi Emeraldine Salt (NMP), however, signal responses were significantly different from the control (blank) at $10^4$ CFU/ml and higher (FIG. 3E, FIG. 3F). While the present example illustrates detection of *B. cereus*, it is to be understood that other microorganisms, or any other analyte of interest can be detected in this manner by utilization of antibodies specific for the analyte of interest.

Discussion.

Selected Conductivities: PANiCNQ conductivity is on the order of $10^3$ μS whereas the solvent NMP conductivity is about 1 μS; thus, the conductive properties arise due to the polymers and not the solvent. PANiCNQ conductivity three weeks after synthesis remained constant ($10^3$ μS), which is significant because it was feared that as the molecule gained magnetic properties and became more structurally ordered (electrons may become localized), the conductive properties might fade.

When PANi was dissolved in NMP without the presence of TCNQ, conductivities were low: 4 μS. From that, it is apparent that TCNQ is a dopant (it is an electron acceptor). When emeraldine base was replaced by emeraldine salt in PANiCNQ synthesis, the resulting compound had similar conductivities to pure PANiCNQ on the order of $10^3$ μS. When PANiCNQ was made in the presence of lactoferrin, the conductance increased slightly, although it was still around $10^3$ μS. The increase in conductivity may be associated with the increase in magnetization.

Conductivities of pure β-carotene in various solutions were too low for the sensitivity of the measuring meter (~0 μS). However, composites of β-carotene with other polymers exhibited much higher conductance. β-carotene (THF)+ PANi emeraldine salt (10% DMF) had a conductivity of 2.5*$10^3$ μS while PANiCNQ+Lactoferrin+β-carotene (THF) had a conductivity of 1.387*$10^3$ μS.

Figure 2C:
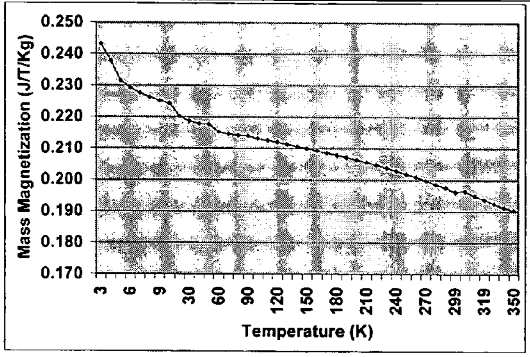
Figure 2D:
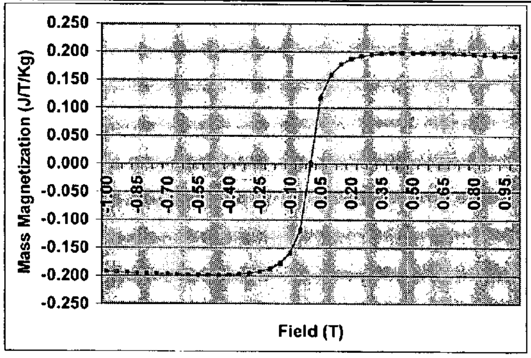
Figure 2E:
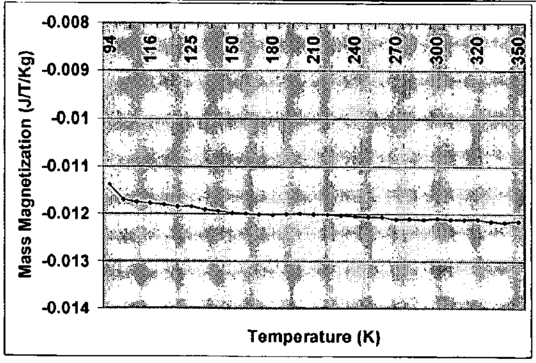
Figure 2F:
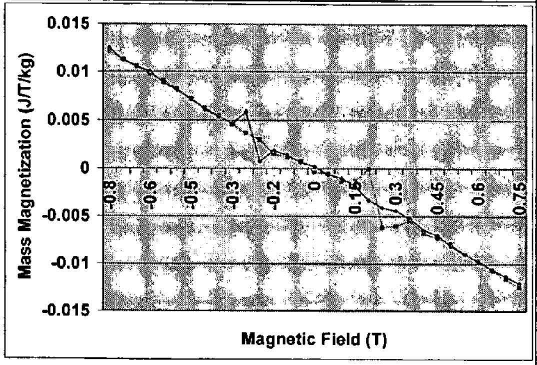

Magnetic properties of PANiCNQ and PANiCNQ-Lactoferrin: From the data, it is apparent that PANiCNQ and PANiCNQ-Lactoferrin are ferri/ferro-magnetic whereas the control emeraldine base is diamagnetic. FIGS. 2A and 2C demonstrate a positive mass magnetization for PANiCNQ and PANiCNQ-Lactoferrin that increases with lower temperatures; the equivalent diagram for emeraldine base PANi, FIG. 2E, shows a negative mass magnetization characteristic of diamagnetic materials. In addition, FIG. 2B for PANiCNQ shows a sigmoidal graph with a magnetic saturation of 0.044 $JT^{-1}Kg^{-1}$, an order higher than previously noted in PANiCNQ studies. FIG. 2C for PANiCNQ-Lactoferrin illustrates a sigmoidal graph with stronger saturation (evidenced by less dipping) equal to 0.2 $JT^{-1}Kg^{-1}$, which is even an order higher than in plain PANiCNQ. Diamagnetic materials have a negative linear graph (FIG. 2F) and paramagnetic materials have a (virtually) positive linear graph that arrives at saturation only at extremely high magnetic fields not used in this study. Remnant magnetization for PANiCNQ was 3.64*$10^{-3}$ T and the coercivity was calculated to be 0.007 T.

Conductometric biosensor performance: Lateral flow of sample through the different membranes (12, 13, 14, 15), which was accomplished by capillary action, was critical for the biosensor 10 signal. As antigen flowed, it interacted with the antibodies on the conjugate pad 13 membrane. These antibodies were conjugated with a variety of polymers (all conductive polymers). As the antigen-antibody-polymer complex flowed through the capture pad 14 membrane, immobilized antibodies on the capture pad 14 membrane also attached to the antigen. The polymer then functions as a molecular wire, connecting the silver electrodes and allowing a current to run through. Unbound sample flows to the absorption pad 15.

Although it would seem natural for conductivity (e.g. resistance drop) to increase as antigen concentration increases, this was not the case in the experiments performed. In the biosensors having antibodies conjugated with PANiCNQ (FIG. 3A, FIG. 3B) and with PANiCNQ+Lactoferrin (FIG. 3C, FIG. 3D), signal response exhibited a parabolic pattern. In the biosensor having antibodies conjugated with β-carotene (THF) and PANi Emeraldine Salt (NMP) (FIG. 3E, FIG. 3F), signal responses exhibit a parabola skewed to the right. The decrease in conductivity at higher concentrations of *B. cereus* may be attributed to a saturation effect where antigens begin to significantly hinder electron transfer.

The sensitivity of the *B. cereus* biosensors with PANiCNQ (+Lactoferrin) is quite good: 149 and 92 CFU/ml, whereas the sensitivity of the sensors with β-carotene and PANi Emeraldine Salt is a bit low: 14600 CFU/ml. Thus, qualitative detection (affirming or denying the presence of antigen at a particular concentration) is certainly no problem. Quantitative detection, on the other hand, requires statistically significant results for signal from one bacterial level to another. At only $1.51 (+$0.025 cents for the reusable copper wafer), each immunosensor is relatively cheap and provides a fast and highly sensitive analysis for bacterial levels.

Conclusion: Here the polymer PANiCNQ was successfully synthesized using a novel approach. After only 3 weeks, the molecule was found to be either ferromagnetic or ferrimagnetic. Mass magnetization measurements at room temperature demonstrate an almost 10-fold increase in magnitude (0.044 $JT^{-1}Kg^{-1}$) compared to previous data on PANiCNQ. The conductivity of PANiCNQ was found to be on the order of $10^{-3}$ S, even as the polymer became more structurally ordered over time. PANiCNQ-lactoferrin demonstrated even strong magnetization when tested at 4 weeks: 0.2 $JT^{-1}Kg^{-1}$ at 300 Kelvin (room temperature), a 10-fold increase over the improved PANiCNQ sample in this study. A variety of PANiCNQ-related molecules were characterized with success as well. Organic magnets are such a recent discovery but have many applications (e.g. information storage and magnetoresistive sensors), thus making advances highly significant.

B-carotene was explored as a conducting polymer with biodegradable properties. Its degradability in toluene was demonstrated in absorbance graphs over several days. While dissolving β-carotene for the formation of nanocomposites, its solubility in kwik-dri was determined to be 500 mg/L. General observations supported the molecule's low conductivity, although an assortment of composites exhibited higher values for conductance.

Both PANiCNQ and PANiCNQ-Lactoferrin were successfully utilized in a newly developed biosensor for *B. cereus* detection with sensitivities around $10^2$ CFU/ml. β-carotene and PANi emeraldine salt were also used in the biosensor with a lower sensitivity around $10^4$ CFU/ml. Consequently, there is considerable support for the use of the magnetic and degradable conductive polymers in a rapid, sensitive, cheap, and portable biosensor. In addition, as a result of the conductive polymer's magnetic properties, the biosensor may be tested more accurately at high dilutions and could potentially be moved by a magnet. The degradability of the biosensor has increased due to the presence of biodegradable polymers. Practical applications of biosensors in fields including pathogen detection, biomedical, and biosecurity are all dominant reasons for biosensor construction and improvement.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for preparing a polymer that is a reaction product of an emeraldine polyaniline (PANi) tetracyanoquinodimethane (TCNQ) and a transferrin family member which comprises:

(a) reacting the PANi and the TCNQ in a solvent at a temperature between about 20° C. and 150° C.;

(b) adding the transferrin family member to the solvent with further heating at a temperature of between about 20° C. and 150° C.; and (c) removing the polymer from the solvent.

2. The process of claim 1, wherein the transferrin is lactoferrin.

3. The process of claim 1, wherein the solvent is N-methyl-2-pyrrolidone (NMP).

4. The process of claim 1, further comprising the step of aging the polymer after step (c) for a time so that the polymer has magnetic properties.

5. The process of claim 1, wherein the polymer is removed from the solvent in step (c) by filtration.

6. The process of claim 1, wherein the polymer also comprises β-carotene.

* * * * *